US005656432A

United States Patent [19]
Claverys et al.

[11] Patent Number: 5,656,432
[45] Date of Patent: Aug. 12, 1997

[54] **GENOMIC DNA FRAGMENT OF *STREPTOCOCCUS PNEUMONIAE*, HYBRIDIZATION PROBE, AMPLIFICATION PRIMER, REAGENT AND METHOD FOR THE DETECTION OF *STREPTOCOCCUS PNEUMONIAE***

[75] Inventors: Jean-Pierre Claverys, Toulouse; Claude Mabilat, Villeurbanne, both of France

[73] Assignee: Bio Merieux, Marcy l'Etoile, France

[21] Appl. No.: 486,137

[22] Filed: Jun. 7, 1995

Related U.S. Application Data

[62] Division of Ser. No. 419,765, Apr. 10, 1995, which is a continuation of Ser. No. 15,850, Feb. 10, 1993, abandoned

[30] Foreign Application Priority Data

Feb. 10, 1992 [FR] France .................. 92 01655

[51] Int. Cl.$^6$ .................................................. C12Q 1/68
[52] U.S. Cl. .................. 435/6; 536/23.7; 536/24.32; 536/24.33
[58] Field of Search .................. 536/23.7, 24.32, 536/24.33; 435/6

[56] References Cited

U.S. PATENT DOCUMENTS 4,683,195  7/1987  Mullis et al. .

FOREIGN PATENT DOCUMENTS

| 0 139 489 | 5/1985 | European Pat. Off. . |
| 0 305 145 | 3/1989 | European Pat. Off. . |
| 2 663 040 | 12/1991 | France . |
| 90-07249 | 12/1991 | France . |
| WO9108305 | 6/1991 | WIPO . |

OTHER PUBLICATIONS

Radnis et al., "Genetic Transformation in *Streptococcus pneumoniae* ... Sequence of recP," *Journal of Bacteriology*, vol. 172, No. 7, Jul. 1990, pp. 3669–3674.

Fenoll et al., "Identification of Atypical Strains of *Streptococcus pneumoniae* by a Specific DNA probe," *European Journal of Clinical Microbiology and Infectious Diseases*, vol. 9, Jun. 1990, pp. 396–410.

Prudhomme, M. et al., "Nucleotide Sequence of the *Streptococcus pneumoniae* hexB Mismatch Repair Gene: Homology of HexB to MutL of *Salmonella typhimurium* and to PMS1 of *Saccharomyces cerevisae*," *J. of Bacteriology*, vol. 171 No., 10, Oct. 1989, pp. 5332–5338.

Alloing, G., et al., "The ami locus of the Gram–positive bacterium *Streptococcus pneumoniae* is similar to binding protein–dependent transport operons of Gram–negative bacteria," *Molecular Microbiology*, (1990), 4(4), 633–644.

Sanger, F., et al., "DNA sequencing with chain-terminating inhibitors (DNA polymerase/nucleotide sequences/bacteriophage øx174)," *Proc. Natl. Acad. Sci. USA*, vol. 74, No. 12, pp. 5436–5467, Dec. 1977 Biochemistry.

Garcia, Pedro, et al., "Nucleotide sequence and expression of the pneumococcal autolysin gene from its own promoter in *Escherichi coli*" *Gene*, 1986 pp. 265–272.

Lefevre, J., et al., "Donor Deoxyribonucleic Acid Length and Marker Effect in Pneumococcal Transformation," *J. of Bacteriology*, Apr. 1979, pp. 80–86, vol. 138, No. 1.

Tiraby, G., et al., "Marker Discrimination in Deoxyribonucleic Acid–Mediated Transformation of Various Pneumococcus Strains," *J. of Bacteriology*, vol. 121, No. 2, Feb. 1975, pp. 608–618.

Cokendall, Alan L., "Classification and Identification of the Viridans Streptococci," *Clinical Microbiology Reviews*, vol. 2, No. 3, Jul. 1989, pp. 315–328.

Kilian, M., et al., "Taxonomic Study of Viridans Streptococci: Description of *Streptococcus gordonii* sp. nov. and Emended Descriptions of *Streptococcus sanguis* (White and Niven 1946), *Streptococcus oralis* (Bridge and Sneath 1982), and *Streptococcus mitis* (Andrews and Horder 1906)," *Intl. J. of Systematic Bacteriology*, vol. 39, No. 4, Oct. 1989, pp. 471–484.

Prere, Marie–Francoise et al., "DNA methylase activities in a *Neisseria gonorrhoeae* extract (In vitro DNA methylation; *Neisseria gonorrhoeae*; gonococcal DNA modification systems)," *FEMS Microbiology Letters* 33, (1986) 37–41.

Haisman, R., et al. "Mutants of *Streptococcus gordonii* Challis over–producing glucosyltransferase," *J. of General Microbiology*, (1991), 137, 483–489.

Kilpper–Balz, R., et al., "Molecular Relationships and Classification of Some Viridans Streptococci as *Streptococcus oralis* and Emended Description of *Streptococcus oralis* (Bridge and Sneath 1982)," *International Journal of Systematic Bacteriology*, vol. 35, No. 4, Oct. 1985, pp. 482–488.

Lewin, Science 237:1570, 1987.

Reeck et al., Cell 50:667, Aug. 28, 1987.

*Primary Examiner*—Scott W. Houtteman
*Attorney, Agent, or Firm*—Oliff & Berridge

[57] ABSTRACT

The invention relates to a fragment of the genomic DNA of *Streptococcus pneumoniae*, a probe capable of specifically hybridizing with the genomic DNA of *Streptococcus pneumoniae*, a specific primer for the amplification, by polymerization, of the genomic DNA, a reagent and a method which are used with the probe and, optionally, the primer, for specifically detecting *Streptococcus pneumoniae* in a biological sample. The probe of the invention is a nucleotide sequence having at least 70% homology with at least a portion of a consensus sequence of the genomic DNA of *Streptococcus pneumoniae*, this consensus sequence being chosen from the nucleotide sequences SEQ ID NO 2, SEQ ID NO 3, SEQ ID NO 4, which are identified in the description, and their respective complementary sequences.

14 Claims, 3 Drawing Sheets

FIG.1a
FIG.1b
FIG.1c

BOX A:
```
hexB  TAATACTCTTCgAAAATCTC.TTCAAACCACGTCAGCGTCGtCTTGCCGTAGATA..GTTg
SII   TAATACTCTTCGAAAATCTC.TTCAAACCACGTCAGCGTCGCCTTaCCGTAGgTATgGTTA
mmsA  TAAcACTtTTCgAAAATCTC.TTCAAACoACGTCAGCtTTGCCTTGCCGTAtATAT.GTTA
comA  TtATACTCTTCGAAAATCaaaTTCAAACCACGTCAgCGTCGCCTTGCCGTAtATAT.GTgA
SI    TAATACTCTTC.........AAACCACGTCAGCtTCaCCTcGCCGTAGgTATgGTTA
ply   TtATACTCTTaGAAAATCTC.TTCAAACCAtGTCAGC.........
             1        10        20        30        40        50     59
CONS. TAATACTCTTCGAAAATCTC.TTCAAACCACGTCAGCGTCGCCTTGCCGTAGATAT.GTTA
```

BOX B:
```
hexB   tTGACTTtGTCAGTTtTATCTACAACCTCAAAACAGTG..TTTTGAa
mmsA4  CTGACTTtGTCAGTctTATCTACAACCTCAAAACAGTG..TTTTGAG
comA   CTGACTTCGTCAGTcCTATCTACAACCTCAAAACAGTG..TTTTGAG
mmsA2  CTGACTTCGTCAGTTCTATCcACAACCTCAAAACAGTG..TTTTGAG
mmsA3  CTGACTTCGTCAGTTCTATCcACAACCTCAAAACAGTG..TTTTGAG
SIII   CTGACTTCGTCAGTTtcATCTACAACCTCAAAACCaTG..TTTTGAG
SII    CTGACTTCGTCAGTTtcATCTACAACCTCAAAACCaTG..TTTTGAG
SII2   CTGACTTCGTCAGTTtcATCcACAACCTCAAAACAGTG..TTTTGAG
SI2    CTGACTTCGTCAGTTCTATCcAtAACtTCAAAACAGTG..TTTTGAG
mmsA1  CTGACTTCGTCAGTTCTATCTgCcACCTCAAAACgGTG..TTTTGAG
lytA   CaGACcTtGTCAGTcCTATtTACAgtgTCAAAAtAGTGcgTTTTGAa
ply    ..........cCTATCcgCAACCTCAAAACAGTG..TTTTGAG
              1        10        20        30        40   45
CONS. CTGACTTCGTCAGTTCTATCTACAACCTCAAAACAGTG..TTTTGAG
```

BOX C:
```
hexB  CtgtCTGCGcCTAGCTTtcTAGTTTGCTCTTTGATTTTtATTGAGTATAc
comA  CAgCCTGCGGCTAGLTTCCTAGTTTGCTCTTTGATTTTCATTGAGTATtA
ply   CAACCTGCGGCTAGCTTtCTAGTTTGCTCTTTGATTTTtATTGAGTATtA
mmsA  CAtCaTGCGGCTAGCTTCtTAGTTTGCTCTTTGATTTTCATTGAGTATAA
SII   CAACCTGCGGCTAGCTTCCTAGTTTGCTCTTTGATTTTCATTGAGTATAA
SI    CAACCTGCGGCTAGCTTCCTAGTTTGCTCTTTaATTTTCATTGAGTATAA
             1        10        20        30        40        50
CONS. CAACCTGCGGCTAGCTTCCTAGTTTGCTCTTTGATTTTCATTGAGTATAA
```

FIG.3

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 340 bases
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: no (i v) ANTI-SENSE: no (v i) ORIGINAL SOURCE:
    (A) ORGANISM: Streptococcus pneumoniae
    (B) STRAIN: R800

(v i i i) POSITION IN GENOME:
    (A) MAP POSITION: 24-26 minutes (i x) FEATURE:
    (A) NAME/KEY: repeating unit
    (B) LOCATION: 3..291
    (C) IDENTIFICATION METHOD: experimentally (x i) SEQUENCE DESCRIPTION: SEQ ID NO:1:

```
GTTAACACTT TTCAAAAATC TCTTCAAACA ACGTCAGCTT TGCCTTGCCG TATATATGTT    60
ACTGACTTCG TCAGTTCTAT CTGCCACCTC AAAACGGTGT TTTGAGCTGA CTTCGTCAGT   120
TCTATCCACA ACCTCAAAAC AGTGTTTTGA GCTGACTTCG TCAGTTCTAT CCACAACCTC   180
AAAACAGTGT TTTGAGCTGA CTTTGTCAGT CTTATCTACA ACCTCAAAAC AGTGTTTTGA   240
GCATCATGCG GCTAGCTTCT TAGTTTGCTC TTTGATTTTC ATTGAGTATA AAAACAGATG   300
AGTTTCTGTT TTCTTTTTAT GGACTATAAA TGTTCAGCTG                         340
```

(2) INFORMATION FOR SEQ ID NO:2:

(i) SEQUENCE CHARACTERISTICS:
        (A) LENGTH: 59 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: no (i v) ANTI-SENSE: no (v i i i) ORIGINAL SOURCE:
        (A) ORGANISM: Streptococcus pneumoniae
        (B) STRAIN: R800

(v i i i) POSITION IN GENOME:
        (A) MAP POSITION:

(i x) FEATURE:
        (A) NAME/KEY: repeating unit
        (B) LOCATION: 1..59
        (C) IDENTIFICATION METHOD: experimentally (x i) SEQUENCE DESCRIPTION: SEQ ID NO:2:

```
TAATACTCTT CGAAAATCTC TTCAAACCAC GTCAGCGTCG CCTTGCCGTA GATATGTTA    59
```

(2) INFORMATION FOR SEQ ID NO:3:

(i) SEQUENCE CHARACTERISTICS:
        (A) LENGTH: 45 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: no (i v) ANTI-SENSE: no (v i) ORIGINAL SOURCE:

(A) ORGANISM: Streptococcus pneumoniae
            (B) STRAIN: R800

(viii) POSITION IN GENOME:
            (A) MAP POSITION:

(ix) FEATURE:
            (A) NAME/KEY: repeating unit
            (B) LOCATION: 1..45
            (C) IDENTIFICATION METHOD: experimentally (xi) SEQUENCE DESCRIPTION: SEQ ID NO:3:

CTGACTTCGT CAGTTCTATC TACAACCTCA AAACAGTG TTTTGAG        45

(2) INFORMATION FOR SEQ ID NO:4:

(i) SEQUENCE CHARACTERISTICS:
            (A) LENGTH: 50 bases
            (B) TYPE: nucleic acid
            (C) STRANDEDNESS: single
            (D) TOPOLOGY: linear (ii) MOLECULE TYPE: DNA (genomic)

(iii) HYPOTHETICAL: no (iv) ANTI-SENSE: no (vi) ORIGINAL SOURCE:
            (A) ORGANISM: Streptococcus pneumoniae
            (B) STRAIN: R800

(viii) POSITION IN GENOME:
            (A) MAP POSITION:

(ix) FEATURE:
            (A) NAME/KEY: repeating unit
            (B) LOCATION: 1..50
            (C) IDENTIFICATION METHOD: experimentally (xi) SEQUENCE DESCRIPTION: SEQ ID NO:4:

CAACCTGCGG CTAGCTTCCT AGTTTGCTCT TTGATTTTCA TTGAGTATAA        50

(2) INFORMATION FOR SEQ ID NO:5:

(i) SEQUENCE CHARACTERISTICS:
            (A) LENGTH: 20 bases
            (B) TYPE: nucleic acid
            (C) STRANDEDNESS: single
            (D) TOPOLOGY: linear (ii) MOLECULE TYPE: DNA (genomic)

(iii) HYPOTHETICAL: no (iv) ANTI-SENSE: no (vi) ORIGINAL SOURCE:
            (A) ORGANISM: Streptococcus pneumoniae
            (B) STRAIN: R800

(viii) POSITION IN GENOME:
            (A) MAP POSITION:

(ix) FEATURE:
            (A) NAME/KEY: repeating unit
            (B) LOCATION: 1..20
            (C) IDENTIFICATION METHOD: experimentally (xi) SEQUENCE DESCRIPTION: SEQ ID NO:5:

ACGTCARCKT YRCCTTRCCG        20

(2) INFORMATION FOR SEQ ID NO:6:

(i) SEQUENCE CHARACTERISTICS:
   (A) LENGTH: 22 bases
   (B) TYPE: nucleic acid
   (C) STRANDEDNESS: single
   (D) TOPOLOGY: linear (ii) MOLECULE TYPE: DNA (genomic)

(iii) HYPOTHETICAL: no (iv) ANTI-SENSE: no (vi) ORIGINAL SOURCE:
   (A) ORGANISM: Streptococcus pneumoniae
   (B) STRAIN: R800

(viii) POSITION IN GENOME:
   (A) MAP POSITION:

(ix) FEATURE:
   (A) NAME/KEY: repeating unit
   (B) LOCATION: 1..22
   (C) IDENTIFICATION METHOD: experimentally (xi) SEQUENCE DESCRIPTION: SEQ ID NO:6:

TATYYACARY STCAAAAYAG TG    22

(2) INFORMATION FOR SEQ ID NO:7:

(i) SEQUENCE CHARACTERISTICS:
   (A) LENGTH: 29 bases
   (B) TYPE: nucleic acid
   (C) STRANDEDNESS: single
   (D) TOPOLOGY: linear (ii) MOLECULE TYPE: DNA (genomic)

(iii) HYPOTHETICAL: no (iv) ANTI-SENSE: no (vi) ORIGINAL SOURCE:
   (A) ORGANISM: Streptococcus pneumoniae
   (B) STRAIN: R800

(viii) POSITION IN GENOME:
   (A) MAP POSITION:

(ix) FEATURE:
   (A) NAME/KEY: repeating unit
   (B) LOCATION: 1..29
   (C) IDENTIFICATION METHOD: experimentally (xi) SEQUENCE DESCRIPTION: SEQ ID NO:7:

TAGTTTGCTC TTTGATTTTY ATTGAGTAT    29

(2) INFORMATION FOR SEQ ID NO:8:

(i) SEQUENCE CHARACTERISTICS:
   (A) LENGTH: 20 bases
   (B) TYPE: nucleic acid
   (C) STRANDEDNESS: single
   (D) TOPOLOGY: linear (ii) MOLECULE TYPE: DNA (genomic)

(iii) HYPOTHETICAL: no (iv) ANTI-SENSE: no (vi) ORIGINAL SOURCE:
   (A) ORGANISM: Streptococcus pneumoniae
   (B) STRAIN: R800

(viii) POSITION IN GENOME:
   (A) MAP POSITION:

```
            ( i x ) FEATURE:
                    ( A ) NAME/KEY: repeating unit
                    ( B ) LOCATION: 1..20
                    ( C ) IDENTIFICATION METHOD: experimentally ( x i ) SEQUENCE DESCRIPTION: SEQ ID NO:8:

ACGTCAGCTT  TGCCTTGCCG                                                                          20

( 2 ) INFORMATION FOR SEQ ID NO:9:

( i ) SEQUENCE CHARACTERISTICS:
                    ( A ) LENGTH: 20 bases
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
                    ( A ) ORGANISM: Streptococcus pneumoniae
                    ( B ) STRAIN: R800

( v i i i ) POSITION IN GENOME:
                    ( A ) MAP POSITION:

( i x ) FEATURE:
                    ( A ) NAME/KEY: repeating unit
                    ( B ) LOCATION: 1..20
                    ( C ) IDENTIFICATION METHOD: experimentally ( x i ) SEQUENCE DESCRIPTION: SEQ ID NO:9:

CGGCAAGGCA  AAGCTGACGT                                                                          20

( 2 ) INFORMATION FOR SEQ ID NO:10:

( i ) SEQUENCE CHARACTERISTICS:
                    ( A ) LENGTH: 20 bases
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
                    ( A ) ORGANISM: Streptococcus pneumoniae
                    ( B ) STRAIN: R800

( v i i i ) POSITION IN GENOME:
                    ( A ) MAP POSITION:

( i x ) FEATURE:
                    ( A ) NAME/KEY: repeating unit
                    ( B ) LOCATION: 1..20
                    ( C ) IDENTIFICATION METHOD: experimentally ( x i ) SEQUENCE DESCRIPTION: SEQ ID NO:10:

ATCTGCCACC  TCAAAACGGT                                                                          20

( 2 ) INFORMATION FOR SEQ ID NO:11:

( i ) SEQUENCE CHARACTERISTICS:
                    ( A ) LENGTH: 20 bases
                    ( B ) TYPE: nucleic acid
                    ( C ) STRANDEDNESS: single
                    ( D ) TOPOLOGY: linear
```

(i i) MOLECULE TYPE: DNA (genomic)

(i i i) HYPOTHETICAL: no (i v) ANTI-SENSE: no (v i) ORIGINAL SOURCE:
    (A) ORGANISM: Streptococcus pneumoniae
    (B) STRAIN: R800

(v i i i) POSITION IN GENOME:
    (A) MAP POSITION:

(i x) FEATURE:
    (A) NAME/KEY: repeating unit
    (B) LOCATION: 1..20
    (C) IDENTIFICATION METHOD: experimentally (x i) SEQUENCE DESCRIPTION: SEQ ID NO:11:

ACCGTTTTGA GGTGGCAGAT    20

(2) INFORMATION FOR SEQ ID NO:12:

(i) SEQUENCE CHARACTERISTICS:
    (A) LENGTH: 20 bases
    (B) TYPE: nucleic acid
    (C) STRANDEDNESS: single
    (D) TOPOLOGY: linear (i i) MOLECULE TYPE: DNA (genomic)

(i i i) HYPOTHETICAL: no (i v) ANTI-SENSE: no (v i) ORIGINAL SOURCE:
    (A) ORGANISM: Streptococcus pneumoniae
    (B) STRAIN: R800

(v i i i) POSITION IN GENOME:
    (A) MAP POSITION:

(i x) FEATURE:
    (A) NAME/KEY: repeating unit
    (B) LOCATION: 1..20
    (C) IDENTIFICATION METHOD: experimentally (x i) SEQUENCE DESCRIPTION: SEQ ID NO:12:

ATCCACAACC TCAAAACAGT    20

(2) INFORMATION FOR SEQ ID NO:13:

(i) SEQUENCE CHARACTERISTICS:
    (A) LENGTH: 20 bases
    (B) TYPE: nucleic acid
    (C) STRANDEDNESS: single
    (D) TOPOLOGY: linear (i i) MOLECULE TYPE: DNA (genomic)

(i i i) HYPOTHETICAL: no (i v) ANTI-SENSE: no (v i) ORIGINAL SOURCE:
    (A) ORGANISM: Streptococcus pneumoniae
    (B) STRAIN: R800

(v i i i) POSITION IN GENOME:
    (A) MAP POSITION:

(i x) FEATURE:
    (A) NAME/KEY: repeating unit
    (B) LOCATION: 1..20
    (C) IDENTIFICATION METHOD: experimentally ( x i ) SEQUENCE DESCRIPTION: SEQ ID NO:13:

ACTGTTTTGA GGTTGTGGAT　　　　　　　　　　　　　　　　　　　　　　　　　　20

( 2 ) INFORMATION FOR SEQ ID NO:14:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
        ( A ) ORGANISM: Streptococcus pneumoniae
        ( B ) STRAIN: R800

( v i i i ) POSITION IN GENOME:
        ( A ) MAP POSITION:

( i x ) FEATURE:
        ( A ) NAME/KEY: repeating unit
        ( B ) LOCATION: 1..20
        ( C ) IDENTIFICATION METHOD: experimentally ( x i ) SEQUENCE DESCRIPTION: SEQ ID NO:14:

ATCTACAACC TCAAAACAGT　　　　　　　　　　　　　　　　　　　　　　　　　　20

( 2 ) INFORMATION FOR SEQ ID NO:15:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
        ( A ) ORGANISM: Streptococcus pneumoniae
        ( B ) STRAIN: R800

( v i i i ) POSITION IN GENOME:
        ( A ) MAP POSITION:

( i x ) FEATURE:
        ( A ) NAME/KEY: repeating unit
        ( B ) LOCATION: 1..20
        ( C ) IDENTIFICATION METHOD: experimentally ( x i ) SEQUENCE DESCRIPTION: SEQ ID NO:15:

ACTGTTTTGA GGTTGTAGAT　　　　　　　　　　　　　　　　　　　　　　　　　　20

( 2 ) INFORMATION FOR SEQ ID NO:16:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no (i v) ANTI-SENSE: no (v i) ORIGINAL SOURCE:
  (A) ORGANISM: Streptococcus pneumoniae
  (B) STRAIN: R800

(v i i i) POSITION IN GENOME:
  (A) MAP POSITION:

(i x) FEATURE:
  (A) NAME/KEY: repeating unit
  (B) LOCATION: 1..20
  (C) IDENTIFICATION METHOD: experimentally (x i) SEQUENCE DESCRIPTION: SEQ ID NO:16:

GAGCATCATG CGGCTAGCTT  20

(2) INFORMATION FOR SEQ ID NO:17:

(i) SEQUENCE CHARACTERISTICS:
    (A) LENGTH: 20 bases
    (B) TYPE: nucleic acid
    (C) STRANDEDNESS: single
    (D) TOPOLOGY: linear (i i) MOLECULE TYPE: DNA (genomic)

(i i i) HYPOTHETICAL: no (i v) ANTI-SENSE: no (v i) ORIGINAL SOURCE:
    (A) ORGANISM: Streptococcus pneumoniae
    (B) STRAIN: R800

(v i i i) POSITION IN GENOME:
    (A) MAP POSITION:

(i x) FEATURE:
    (A) NAME/KEY: repeating unit
    (B) LOCATION: 1..20
    (C) IDENTIFICATION METHOD: experimentally (x i) SEQUENCE DESCRIPTION: SEQ ID NO:17:

AAGCTAGCCG CATGATGCTC  20

(2) INFORMATION FOR SEQ ID NO:18:

(i) SEQUENCE CHARACTERISTICS:
    (A) LENGTH: 20 bases
    (B) TYPE: nucleic acid
    (C) STRANDEDNESS: single
    (D) TOPOLOGY: linear (i i) MOLECULE TYPE: DNA (genomic)

(i i i) HYPOTHETICAL: no (i v) ANTI-SENSE: no (v i) ORIGINAL SOURCE:
    (A) ORGANISM: Streptococcus pneumoniae
    (B) STRAIN: R800

(v i i i) POSITION IN GENOME:
    (A) MAP POSITION:

(i x) FEATURE:
    (A) NAME/KEY: repeating unit
    (B) LOCATION: 1..20
    (C) IDENTIFICATION METHOD: experimentally (x i) SEQUENCE DESCRIPTION: SEQ ID NO:18:

GCTAGCTTCT TAGTTTGCTC  20

( 2 ) INFORMATION FOR SEQ ID NO:19:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
        ( A ) ORGANISM: Streptococcus pneumoniae
        ( B ) STRAIN: R800

( v i i i ) POSITION IN GENOME:
        ( A ) MAP POSITION:

( i x ) FEATURE:
        ( A ) NAME/KEY: repeating unit
        ( B ) LOCATION: 1..20
        ( C ) IDENTIFICATION METHOD: experimentally ( x i ) SEQUENCE DESCRIPTION: SEQ ID NO:19:

GAGCAAACTA AGAAGCTAGC        20

( 2 ) INFORMATION FOR SEQ ID NO:20:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
        ( A ) ORGANISM: Streptococcus pneumoniae
        ( B ) STRAIN: R800

( v i i i ) POSITION IN GENOME:
        ( A ) MAP POSITION:

( i x ) FEATURE:
        ( A ) NAME/KEY: repeating unit
        ( B ) LOCATION: 1..20
        ( C ) IDENTIFICATION METHOD: experimentally ( x i ) SEQUENCE DESCRIPTION: SEQ ID NO:20:

TGCTCTTTGA TTTTCATTGA        20

( 2 ) INFORMATION FOR SEQ ID NO:21:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( v i ) ORIGINAL SOURCE:
        ( A ) ORGANISM: Streptococcus pneumoniae
        ( B ) STRAIN: R800

(viii) POSITION IN GENOME:
   (A) MAP POSITION:

(ix) FEATURE:
   (A) NAME/KEY: repeating unit
   (B) LOCATION: 1..20
   (C) IDENTIFICATION METHOD: experimentally (xi) SEQUENCE DESCRIPTION: SEQ ID NO:21:

TCAATGAAAA TCAAAGAGCA 20

GENOMIC DNA FRAGMENT OF *STREPTOCOCCUS PNEUMONIAE*, HYBRIDIZATION PROBE, AMPLIFICATION PRIMER, REAGENT AND METHOD FOR THE DETECTION OF *STREPTOCOCCUS PNEUMONIAE*

This is a Division of application Ser. No. 08/419,765 filed Apr. 10, 1995, which in turn is a Continuation of application Ser. No. 08/015,850, filed Feb. 10, 1993 now abandoned.

BACKGROUND OF THE INVENTION

The present invention relates to a genomic DNA fragment of the bacterium *Streptococcus pneumoniae*, a probe capable of specifically hybridizing with the genomic DNA of *Streptococcus pneumoniae*, a primer for specifically amplifying the genomic DNA of *Streptococcus pneumoniae*, a reagent and a method for selectively detecting, in a biological sample, said bacterium, used with the probe of the invention.

Research studies have been carried out on the isolation of two nucleotide fragments, on their sequencing, their specificity towards the genomic DNA of *Streptococcus pneumoniae* and their use for the production of hybridization probes intended for a diagnostic method.

These two fragments are respectively the hexB gene, deposited and accessible at the gene library of EMBL (European Molecular Biology Laboratory, Heidelberg, Germany) under the number M29686 and the study of which was especially the subject of the publication by M. PRUDHOMME, B. MARTIN, V. MEJEAN and J. P. CLAVERYS (1989) J. Bacteriol. 171, 5332–5338 and which encodes an essential protein of the system for the mismatch repair of the *Streptococcus pneumoniae* DNA, and the ami operon, deposited and accessible at the gene library of EMBL under the number X17337 and the study of which has especially been the subject of the publication by G. ALLOING, M. C. TROMBE and J. P. CLAVERYS (1990 Mol. Microbiol., 4, 633–644, and which is involved in the transport of oligopeptides in pneumococcus.

For each of these two fragments, various sub-fragments were prepared and used as hybridization probes for the genomic DNA of *Streptococcus pneumoniae*. The most commonly used probes are, in the case of the hexB gene, the hexB-$S_7$ fragment obtained by the action of the restriction enzymes HindIII-BglII (from nucleotide 1321 to nucleotide 1776) containing 455 nucleotides, and, in the case of the ami operon, the ami-$S_2$ fragment obtained by the action of the restriction enzymes BamHI-EcoRI (from nucleotide 2419 to nucleotide 3564), containing 1145 nucleotides.

Each of these two probes was subjected to hybridization experiments according to the so-called "dot-blot" technique according to MANIATIS et al. (1982), Molecular Cloning, Cold Spring Harbor, with the genomic DNA of *Streptococcus pneumoniae* and the genomic DNA of other genera and species of bacteria, under stringent conditions (50% formamide, at 42° C.), on nylon membranes (trade name Biodyne A, from the company Pall), using two concentrations of respectively 10 ng and 100 ng of genomic DNA.

Identical results were obtained with the two probes hexB-$S_7$ and ami-$S_2$. FIG. 1 shows the results obtained with the probe ami-$S_2$ previously labeled by radioactive labeling with $^{32}P$ (trade name Kit Multiprime from the company Amersham), the hybridizations being visualized by autoradiography, for 12 hours at −70° C. According to FIG. 1, two DNA spots of respectively 10 ng (dotted arrow) and 100 ng (solid arrow) were prepared for each of the bacterial strains used. The bacterial strains were grouped together by series and numbered within each series as follows:

a series:

a1–a11: Clinical isolates of *Streptococcus pneumoniae* belonging to different serotypes.

b series:

b1–b5: *Streptococcus oralis* of the API collection (BioMérieux SA) (internal references API No. 7902025, 7902072, 8305023, 8040010, accessible at National Culture Type Collection under the reference NCTC11427, 8408077).

b6–b10: Clinical isolates classified *Streptococcus sanguis* based on API-20 Strep tests (BioMérieux SA) of which the result is indicated in brackets below in the order, SI (4061440), SII (0260451), SII (0270441), SI (0061440), SII (0240440).

b11–b12: Clinical isolates classified *Streptococcus mitis* based on the API-20 Strep tests (0040401 for both strains).

b13–b14: Clinical isolates classified *Streptococcus milleri* based on the API-20 Strep tests (1061010 for both strains).

b15–b16: Clinical isolates classified *Streptococcus salivarius* based on the API-20 Strep tests (5060451 and 5060461).

b17–b20: Clinical isolates of *Enterococcus faecalis, Listeria monocytogenes, Haemophilus influenzae* and *Neisseria meningitidis*.

c series:

c: "Atypical streptococci" obtained from clinical isolates.

According to FIG. 1, the results are as follows:

All the strains of *Streptococcus pneumoniae* of the a) series give very visible signals which are proportional to the concentration considered.

The atypical streptococci of the c, c91, c120, c108, c108, c92, c188, c139, c155, c184, c115, c65 and c174 series give the same signals as those of the a) series and could therefore be classified, based on this test, in the *Streptococcus pneumoniae* species.

All the strains of *Streptococcus oralis* of the b) series, with the exception of the b5 strain, the strain *Streptococcus mitis* b11 and the atypical streptococci of the c, c185, c160 and c85 series, give a visible signal for the concentration of 100 ng, the intensity of the signal being about 10 times weaker than that obtained for *Streptococcus pneumoniae* at the same concentration.

These results therefore demonstrate the lack of specificity respectively of the probes hexB-$S_7$ and ami-$S_2$ for *Streptococcus pneumoniae*, within the genus Streptococcus since a partial, but nevertheless significant, hybridization is detected with the species *Streptococcus oralis*, the closest species to *Streptococcus pneumoniae* and *Streptococcus mitis*. These probes are therefore unsatisfactory for the production of a selective test for detecting *Streptococcus pneumoniae* among other bacterial species which are most closely related.

In conformity with the publication by A. FENOLL, J. V. MARTINEZ-SUAREZ, R. MUNOZ, J. CASAL and J. L. GARCIA, Eur. J. Clin. Microbiol. Infect. Dis., 9 (June 1990) 396–401, other research studies led to the preparation of a hybridization probe (pCE3) for the genomic DNA of *Streptococcus pneumoniae* which is a 650-base pair fragment isolated from the lyt A gene, the latter encoding the N-terminal end of the streptococcal autolysin, amidase.

This probe was tested on 44 streptococcal strains among which 27 were identified as atypical streptococci strains and the other 17 as strains of *Streptococcus viridans*, based on conventional identification tests.

Although this probe provides a solution to the problem of the identification of *Streptococcus pneumoniae*, and in particular among atypical streptococci, it has, nevertheless, two disadvantages:

the probe used is a 650-base pair fragment and its production industrially is therefore not easy, and, in particular, the specificity of this probe is entirely linked to the presence of the lyt A gene, of which the copy in the genomic DNA of *Streptococcus pneumoniae* is unique; therefore, it will not be able to detect or identify a strain of *S. pneumoniae* from which the lyt A gene has been deleted; furthermore, this small number of copies is a disadvantage for the detection by direct hybridization and for the amplification of the target DNA.

SUMMARY OF THE INVENTION

The present invention aims to solve the above-mentioned problems of selective detection of *Streptococcus pneumoniae*, especially those encountered in medical bacteriology.

The first subject of the invention is a single-stranded fragment of the genomic DNA of *Streptococcus pneumoniae* comprising at least one nucleotide sequence having at least 70% homology with at least one nucleotide sequence chosen from the nucleotide sequences SEQ ID NO 2, SEQ ID NO 3, SEQ ID NO 4, which are represented at the end of the description, and their respective complementary sequences. Complementary sequence is understood to mean any sequence which completely hybridizes with the sequence represented. Fragment is understood to mean a piece of DNA which is detached, isolated or broken off from genomic DNA.

Preferably, the nucleotide sequence of the fragment according to the invention has at least 85% homology with at least one of said nucleotide sequences.

The single stranded fragment can consist essentially of at least one nucleotide sequence which is at least 70% homologous and preferably at least 85% homologous to at least one or to one nucleotide sequence selected from the group consisting of the nucleotide sequences SEQ ID NO 2, SEQ ID NO 3, SEQ ID NO 4 and their respective complementary sequences.

A second subject of the invention directly uses said fragment and consists of a probe which is capable of specifically hybridizing with the genomic DNA of *Streptococcus pneumoniae*, said probe comprising a nucleotide sequence having at least 70% homology with at least a portion of a consensus sequence of the genomic DNA of *Streptococcus pneumoniae*, this consensus sequence being chosen from the nucleotide sequences SEQ ID NO 2, SEQ ID NO 3, SEQ ID NO 4 and their respective complementary sequences.

Preferably, the nucleotide sequence of the probe of the invention has at least 85% homology with at least a portion of said consensus sequence.

The probe of the invention advantageously comprises at least 12 nucleotides.

Preferably, the probe of the invention comprises the nucleotide sequence SEQ ID NO 3.

When it comprises SEQ ID NO 3, it may be flanked at its 5' end by the nucleotide sequence SEQ ID NO 2 and/or at its 3' end by the nucleotide sequence SEQ ID NO 4.

The nucleotide sequence SEQ ID NO 3 may be repeated, and it is, advantageously four times contiguously.

According to the invention, a probe may have a shorter nucleotide sequence and be chosen from the sequences SEQ ID NO 5, SEQ ID NO 6 and SEQ ID NO 7, which are presented at the end of the description.

The labeling of the probe does not influence its specificity with respect to the genomic DNA of *Streptococcus pneumoniae* and an appropriate marker is preferably chosen from radioactive isotopes, from enzymes chosen from peroxidase and alkaline phosphatase and those capable of hydrolyzing a chromogenic, fluorigenic or luminescent substrate, from chromophoric chemical compounds, from chromogenic, fluorigenic or luminescent compounds, from nucleotide base analogs and from biotin.

In order to use a probe of the invention in vivo, its molecular structure is chemically modified. Appropriate chemical modifications, which make it possible to increase the stability to enzymatic degradation, especially due to nucleases, and additionally to increase the hybridization yield, do not of course affect the sequence of bases. Examples thereof are the introduction, between at least two nucleotides, of a group chosen from diphosphate esters, from alkyl- and aryl-phosphonate and from phosphorothioate, or the replacement of at least one deoxyribose by a polyamide.

A third subject of the invention is a primer for the specific polymerization of the genomic DNA of *Streptococcus pneumoniae* so as to obtain an amplification of the latter. This primer comprises a nucleotide sequence having at least 70% homology with at least a portion of a consensus sequence of the genomic DNA of *Streptococcus pneumoniae*, this consensus sequence being chosen from the nucleotide sequences SEQ ID NO 2, SEQ ID NO 3, SEQ ID NO 4 and their respective complementary sequences.

Preferably, the nucleotide sequence of a primer of the invention is chosen from the sequences SEQ ID NO 8 to SEQ ID NO 21, which are represented at the end of the description.

Depending on the amplification techniques considered, it is preferable to use a pair of primers comprising at least one primer of the invention.

In the case where the pair consists of two primers of the invention, said pair is advantageously chosen from the pairs of primer consisting of a primer of the nucleotide sequence SEQ ID NO 8 and a primer of any one of the nucleotide sequences SEQ ID NO 11, SEQ ID NO 13, SEQ ID NO 15, SEQ ID NO 17, SEQ ID NO 19 and SEQ ID NO 21, and from the pairs of primer consisting of a primer of the nucleotide sequence SEQ ID NO 10 and a primer of any one of the nucleotide sequences SEQ ID NO 13, SEQ ID NO 15, SEQ ID NO 19 and SEQ ID NO 21.

A fourth subject of the invention is a reagent for selectively detecting *Streptococcus pneumoniae* in a biological sample, using a probe of the invention as described above.

If the hybridization technique considered is the so-called sandwich technique, the reagent of the invention comprises a capture probe and a detection probe having the characteristics of a probe of the invention, the detection probe being especially labeled by means of one of the markers described above. Capture probe refers to any polynucleotide fixed upon a macromolecular support, capable of hybridizing with a portion (or capture region) of a nucleic acid to be detected in a sample (target), in particular DNA. The capture probe may be a natural nucleic acid fragment (in particular DNA), a natural or synthetic oligonucleotide or a synthetic nucleic acid fragment (in particular DNA) which is unmodified or containing one or more modified bases such as inosine, 5-methyldeoxycytidine, deoxyuridine, 5-dimethylaminodeoxyuridine, 2,6-diaminopurine, 5-bromodeoxyuridine or any other modified base which allows the hybridization.

Appropriate chemical modifications which make it possible to increase the stability to enzyme degradation and enhance the hybridisation yield may also be envisaged, such as for example the introduction, between at least two nucleotides, of a group chosen from diphosphate, alkyl- or acylphosphonate and phosphorothioate esters, or the replacement of at least one deoxyribose by a polyamide. The detection probe is a probe capable of hybridising with a portion of the target (detection region) which corresponds to the definition above and is labeled by means of any appropriate marker chosen from enzymatic markers, preferably from horseradish peroxydase, alkaline phosphotase or any enzyme capable of hydrolysing a chromogenic, fluorigenic or luminiscent substrate; radioactive isotopes, chromophoric chemical compounds; chromogenic, fluorigenic or luminiscent compounds, or anologs of nucleotide bases and biotin. In the reagent, the probe of the invention is in liquid medium or is directly or indirectly fixed on a solid support. Said support is in any appropriate form such as a tube, cone, well, microtiter plate, sheet, or soluble polymer. It consists of a natural or synthetic material, modified chemically or otherwise, and is, depending on the technique adopted, chosen from polystyrenes, styrene/butadiene copolymers, styrene/butadiene copolymers mixed with polystyrenes, polypropylenes, polycarbonates, polystyrene/acrylonitrile copolymers, styrene-methyl methacrylate copolymers, from synthetic nylon and natural fibers, from polysaccharides and cellulose derivatives.

Furthermore, the reagent of the invention may contain at least one primer as described above, so as to allow an amplification technique to be performed before the selective detection of Streptococcus pneumoniae and it preferably contains a pair of primers according to the invention.

The final subject of the present invention is a method for the selective detection of Streptococcus pneumoniae in a biological sample, consisting in exposing the genomic DNA of the bacteria contained in said sample, in the form of single-stranded fragments, to a probe of the invention, and then in detecting the regions of hybridization with said probe.

Most known hybridization techniques can be used in this method, and especially the so-called dot-blot, Southern and sandwich hybridization techniques. To carry out the latter technique, the method consists in previously exposing the genomic DNA of the bacteria in the sample to a capture probe of the invention, upon which the genomic DNA of the Streptococcus pneumoniae will bind specifically, and then in exposing the bound DNA to a detection probe of the invention.

According to the invention, the method advantageously comprises a stage for the amplification of the genomic DNA of Streptococcus pneumoniae, in the presence of an appropriate enzymatic system and at least one primer and especially a pair of primers of the invention, prior to the stage for the detection of Streptococcus pneumoniae.

The development of the invention and its usefulness are now set out according to stages 1 to 4 and in support of FIGS. 2 and 3:

BRIEF DESCRIPTION OF THE DRAWINGS

Figures 1A, 1B, 1C:
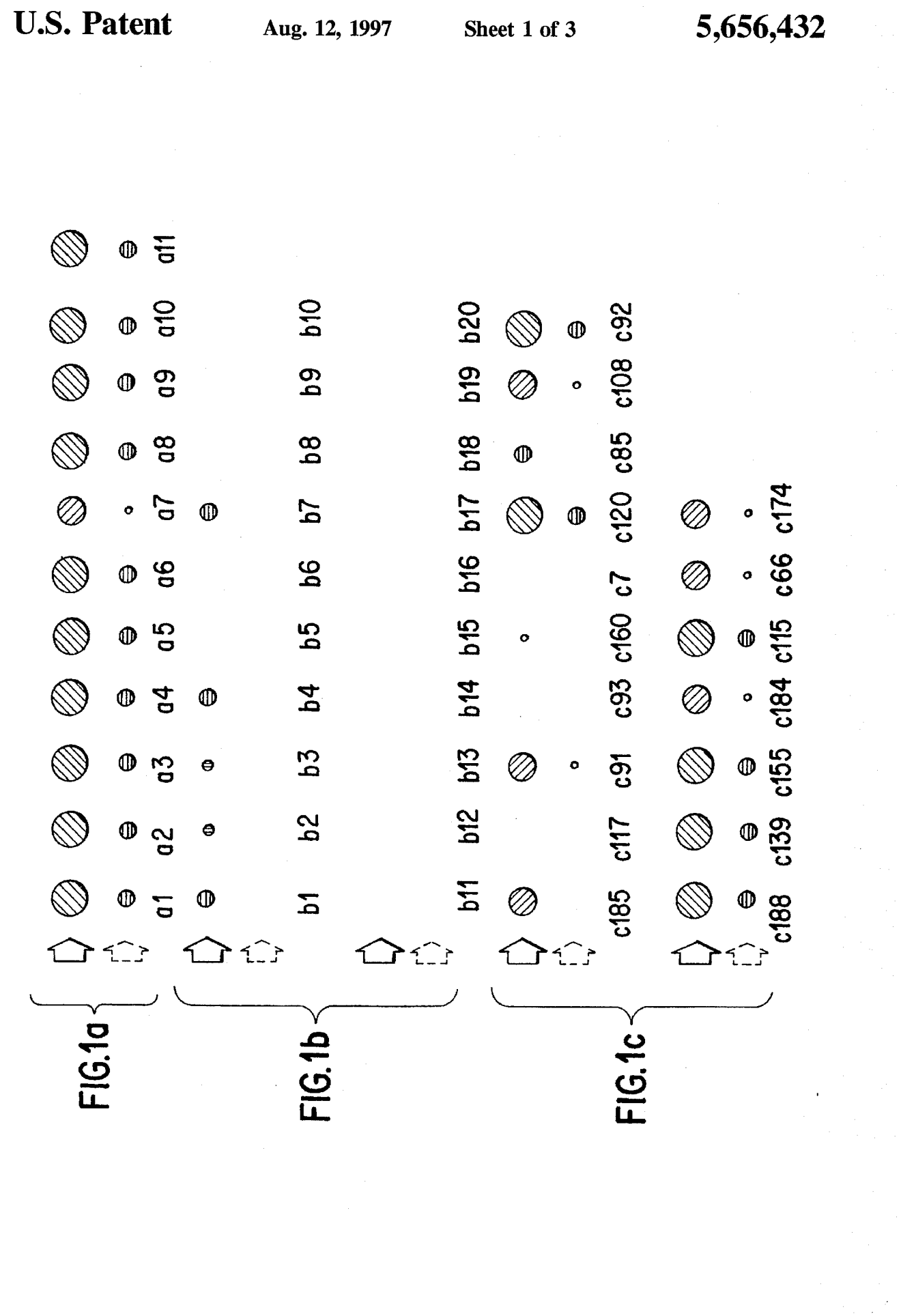

FIG. 1 shows results obtained with the probe ami-$S_2$, labeled by radioactive $^{32}P$, FIG. 2, makes it possible to locate, in the vicinity of the various Streptococcus pneumoniae genes, the repetitive nucleotide sequences called boxA, boxB and boxC respectively.

FIG. 3 illustrates the determination of the consensus sequences SEQ ID NO 2, SEQ ID NO 3 and SEQ ID NO 4 respectively, by alignment of the various repetitive sequences in the vicinity of 5 Streptococcus pneumoniae genes.

DESCRIPTION OF PREFERRED EMBODIMENTS

Figure 2:
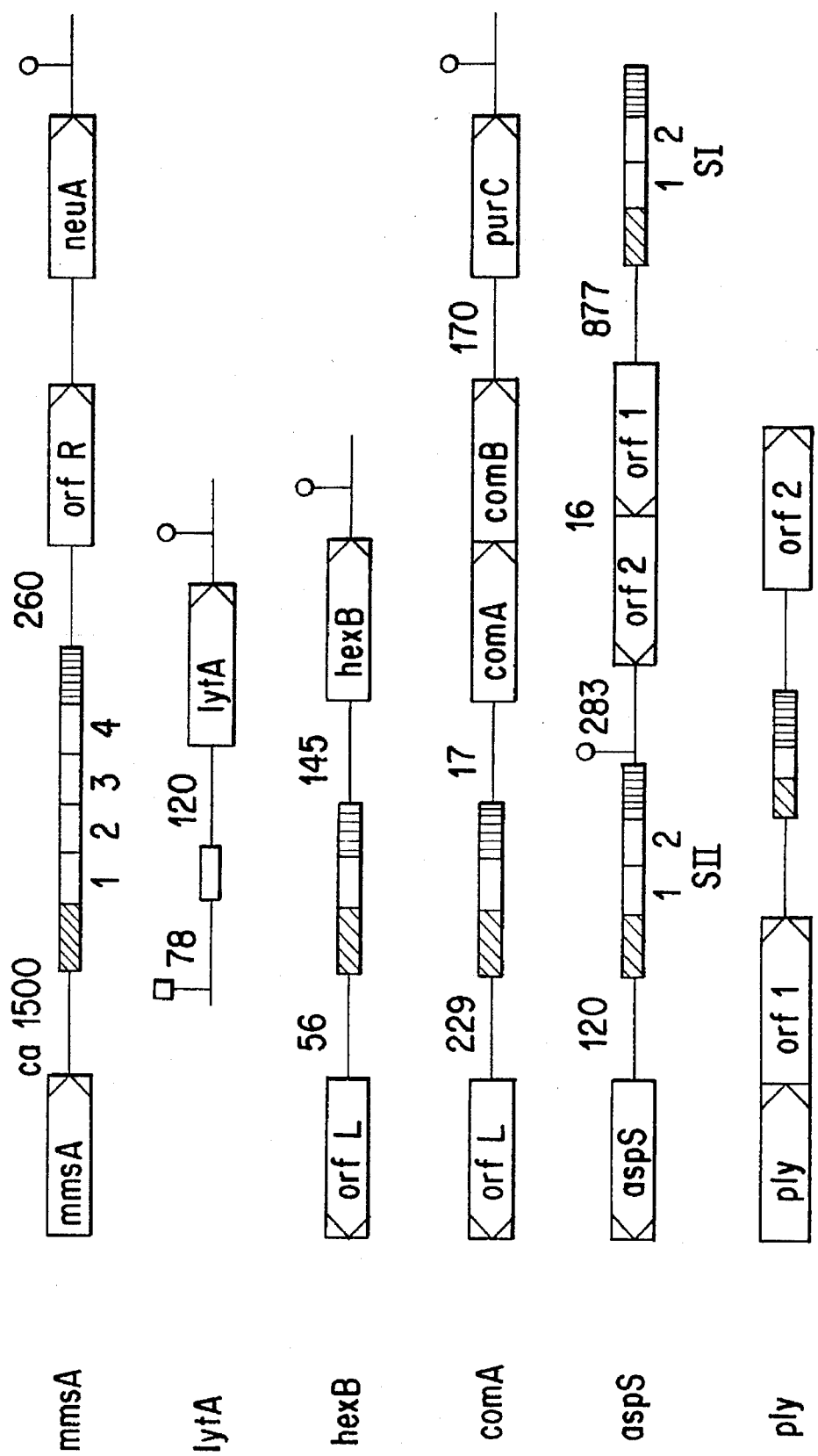
FIG. 2 shows the organization of the BOX sequences and their positions relative to identified flanking genes or open reading frames and their transcriptional signals. BoxA, boxB and boxC are indicated by black-, open- and shaded-rectangles, respectively. Each copy of boxB at the same locus is numbered below the line for identification in FIG. 3. SI and SII indicate leftside and rightside BOX elements in he aspS fragment, respectively. Coding regions and their direction of transcription are denoted by open rectangles with an arrow. Vertical bars with an open circle denote a rho-independent terminator having a stem-loop structure that blocks transcription. The lytA promoter is indicated by a vertical bar with an open square. Base pair distances between the coding regions, elements and transcription initiation and termination signals are indicated above each line.

STAGE 1—Isolation of a repetitive sequence in the genomic DNA of Streptococcus pneumoniae The isolation, using genetic recombination techniques in vitro during extensive work on the study of Streptococcus pneumoniae, of a genomic DNA sequence made it possible to identify, by means of the technique of hybridization with total DNA according to the SOUTHERN technique, a fragment exhibiting homology with several other genomic fragments. This situation results in the generation of 20 to 25 fragments. This fragment was found, experimentally, to be specific for Streptococcus pneumoniae. The determination of its sequence made it possible to identify a new gene designated mmsA which may be involved in the molecular mechanisms of DNA repair and recombination.

A specific sequence responsible for these multiple hybridizations was localized in this fragment. It is a nucleotide sequence situated in the region downstream, in the 5'→3' direction, of the mmsA gene. This sequence, which is obtained by the action of the restriction enzymes HpaI and PvuII, has 340 base pairs, according to the SEQ ID NO 1 given at the end of the description. The complete nucleotide sequence of the two complementary strands of this fragment was determined by the chain termination method (according to SANGER et al., Proc. Natl. Acad. Sci. USA, 1977, 74, 5463–5467) using single-stranded DNA templates of the phage M13. The existence, inside this sequence, of a 45-nucleotide sequence called boxB, directly repeated 4 times, was thus demonstrated.

This boxB sequence was subsequently also found, by sequence comparison, in regions upstream of the hexB, comA, lytA, ply, SI, SII genes. It was observed that these copies of boxB could be flanked in 5' and in 3' by sequences containing about fifty nucleotides, which are also conserved, and are called boxA and boxC respectively. A consensus sequence was determined for each of these boxes, A, B and C respectively, by alignment of the different nucleotide sequences of the hexB, comA, lytA, ply, SI and SII regions, which corresponds to the nucleotide chain most frequently found in these regions. The consensus sequences SEQ ID NO 2, SEQ ID NO 3 and SEQ ID NO 4 correspond to the boxes, A, B and C respectively.

Organization and Chromosomal Location

The general organization of these repetitive regions in the genomic DNA of *Streptococcus pneumoniae* is schematically represented in FIG. 2.

The chromosome sites containing the sequences situated in the vicinity of the hexB, comA, lytA and mmsA genes have been characterized. These sites are located at different points on the chromosome map of *Streptococcus pneumoniae* established by separation of DNA fragments by pulse field electrophoresis (Gasc et al., 1991). Adopting a circular representation for this map, based on an arbitrary division into 60 minutes, with a 0/60 position situated at the top of the circle, and a clockwise direction, the location, expressed in minutes, of various fragments is, for the test strain:

comA: 7'
hexB: 10–11'
lytA: 21–24'
mmsA: 24–26'

This observation suggests that fragments containing these repetitive regions have completely different chromosomal locations.

This situation is very advantageous since it ensures that, even in the event of a substantial chromosome rearrangement, many copies of this repetitive sequence are conserved in the genomic DNA.

STAGE 2—Development of the probes of the invention

Sequence alignments between the various copies identified were performed by computer processing. These alignments made it possible to obtain the consensus sequences described above for the copies of boxA, boxB and boxC. These consensus sequences are given at the end of the description by the references SEQ ID NO 2, SEQ ID NO 3 and SEQ ID NO 4 respectively.

According to FIG. 3, these alignments made it possible to define the sequence and location of three oligodeoxyribonucleotides indicated at the end of the description by the references SEQ ID NO 5, SEQ ID NO 6 and SEQ ID NO 7 respectively. One of these oligonucleotides is derived from the alignment of the copies of boxA (SEQ ID NO 5). The second oligodeoxyribonucleotide (SEQ ID NO 6) is derived from the alignment of the copies of boxB, a third (SEQ ID NO 7) is derived from the alignment of the copies of boxC. These oligodeoxyribonucleotides, as well as any other consensus sequence established from the data for boxA, boxB and boxC, or any other sequence exhibiting at least 70% homology with one of the consensus sequences, can be used as specific probe for the genomic DNA of *Streptococcus pneumoniae*.

STAGE 3—Determination of specificity by molecular hybridization using the probes SEQ ID NO 6 and SEQ ID NO 7 a) Choice of the bacterial strains:

The classification of the bacterial strains used is specified below:

1. Laboratory strain R800 of *Streptococcus pneumoniae* (Lefèvre, J. C., Claverys, J. P., and Sicard, A. M. (1979) J. Bacteriol. 138, 80–86), derived from the strain R36A (Tiraby, G., Fox, M. S., and Bernheimer, H. (1975) J. Bacteriol. 121, 608–618).
2. Atypical clinical isolate (101/87), lacking a capsule, resistant to optochin, resistant to lysis by DOC, but lytA$^+$.
3. Strain GM99 of *Escherichia coli* (Prère, M. -F. and Fayet, O. (1986) Microbiol. Lett. 33, 37–41).
4. Clinical isolate classified *Streptococcus sanguis* II (API-20 Strep 0260451), resistant to optochin, pneumolysin negative.
5. Clinical isolate classified *Streptococcus sanguis* II (API-20 Strep 0270441), average resistance to optochin, pneumolysin negative.
6. Strain OB11 of *Streptococcus gordonii* (ex *Streptococcus sanguis* Challis (Haisman, R. J. and Jenkinson, H. F. 1991. Mutants of *Streptococcus gordonii* Challis overproducing glucosyltransferase. J. Gen. Microbiol. 137, 483–489), biovar 2 according to Kilian et al. (Kilian et al., 1989).
7. Clinical isolate classified *Streptococcus mitis* (API-20 Strep 0040401).
8. Clinical isolate classified *Streptococcus mitis* (API-20 Strep 0040401).
9. Strain of *Streptococcus oralis*, API SYSTEM collection (ref. No. 7902072).
10. Strain NCTC 11427 of *Streptococcus oralis* (Ronda et al., 1988).
11. Clinical isolate of *Streptococcus pneumoniae* (serotype 18).
12. Clinical isolate of *Streptococcus pneumoniae* (serotype 6) .
13. Clinical isolate of *Streptococcus pneumoniae* (serotype 23).

Among the streptococcal species, the results of DNA-DNA hybridization (Kilpper-Bälz, R., Wenzig, P., and Schleifer, K. H. 1985. Molecular relationships and classification of some viridans streptococci as *Streptococcus oralis* and amended description of *Streptococcus oralis* (Bridge and Sneath 1982) Int. J. Sys. Bact. 35, 482–488) show that *Streptococcus oralis*, which comprises various strains previously classified as *S. sanguis* II, *S. mitior, S. viridans*, and *S. mitis* are the two species most closely related to *Streptococcus pneumoniae*. The NCTC 11427 strain of *Streptococcus oralis* selected for this study is the typical strain (Kilpper-Bälz et al., 1985, and Coykendall, A. L. 1989, Classification and identification of Viridans Streptococci. Clin. Microbiol. Rev. 2, 315–328, Kilian, M., Mikkelsen, L., and Henrichsen, H. 1989, Taxonomic study of Viridans Streptococci: description of *Streptococcus gordonii* sp. nov. and amended descriptions of *Streptococcus sanguis* (White and Niven 1946) , *Streptococcus oralis* (Bridge and Sneath 1982); and *Streptococcus mitis* (Andrewes and Horder, 1906), Int. J. Sys. Bact. 39, 471–484). It was in fact from this strain that the DNA fragment which constitutes a specific probe for *Streptococcus oralis* was isolated (Schmidhuber et. al., 1988). *Streptococcus mitis* is represented by two clinical isolates.

*Streptococcus gordonii*, a newly created species (Kilian et. al., 1989) which includes many strains previously classified as *S. sanguis* II, represented by the strain OB11 (ex *S. sanguis* Challis) (Kilian et. al., 1989, Haisman and Jenkinson, 1991), as well as *S. sanguis*, which is not represented in this study, can be considered, based on the results of DNA-DNA hybridization, as less closely related to *Streptococcus pneumoniae* than *Streptococcus oralis* and *Streptococcus mitis*.

The results of the DNA-DNA hybridization experiments are demonstrated in Kilpper-Bälz et. al. (1985), in which is represented at least one typical strain of each of these species.

b) Preparation of the samples, gel electrophoresis and transfer onto nylon membrane:

Chromosomal DNA of the various streptococcal strains was prepared by the technique described by Fenoll et. al. (1990). The enzymatic digestion by the enzyme PstI as well as the agarose gel electrophoresis and the transfers onto charged nylon membrane (Biodyne B, from PALL) were carried out under the conditions described by Maniatis, T., Fristsch, E. F., and Sambrook (1982), Molecular cloning; A laboratory manual (Cold Spring Harbor, N.Y.: Cold Spring Harbor Laboratory).

c) Molecular hybridization conditions:

The oligodeoxyribonucleotide was labeled in 5' by T4 bacteriophage DNA kinase (from Bethesda Research Laboratory) using [γ-$^{32}$p]ATP (at 3000 Ci/mM). 50 µl of solution of labeled oligonucleotide (1×10$^7$ cpm for about 2.5 picomoles) were introduced into a hybridization buffer [6× SSC (saline sodium citrate), 10× Denhardt's, 0.1% SDS (Na dodecyl sulfate)], (50 mg/ml salmon sperm DNA, 1% of Boehringer blocking reagent) (Maniatis et. al., 1982). The hybridization was performed at 40° C. (probe SEQ ID NO 6) or 48° C. (probe SEQ ID NO 7), for about 15 hours. After two brief washes in a solution of 6× SSC, 0.1% SDS, at room temperature, the membrane was placed in contact with an X-ray film which had been exposed for 3 to 36 hours at −70° C.

An experiment for the identification of *Streptococcus pneumoniae* by molecular hybridization was performed using, as probe, the oligonucleotides (SEQ ID NO 6 and SEQ ID NO 7). Chromosomal DNAs from *Streptococcus pneumoniae* and other streptococci, including *Streptococcus oralis* and *Streptococcus gordonii*, two of the species most closely related to this bacterium, were digested with the restriction enzyme PstI, separated by agarose gel electrophoresis and then transferred onto nylon membrane. The $^{32}$P-labeled oligonucleotide was placed in contact with this membrane, under standard hybridization conditions.

The hybridization results show very strong hybridization signals obtained with the DNA of *Streptococcus pneumoniae*, whereas they are nonexistent with the DNA of *Streptococcus oralis*, the species most closely related to *Streptococcus pneumoniae*, as well as with the DNA of *Streptococcus gordonii*, of clinical isolates classified as *Streptococcus sanguis*, and of one of the clinical isolates classified as *Streptococcus mitis*.

STAGE 4—Identification of *Streptococcus pneumoniae* by direct colony hybridization using a nonradioactive and semi-automated detection system described in French Patent No. 90 07249 whose content is incorporated into the present description, where appropriate.

The identification of the *Streptococcus pneumoniae* strains from the strains described in stage 3 was confirmed based on this nonradioactive detection technology.

The extraction of total DNA from colonies was carried out in the following manner. A bacterial colony standardized as a 10$^9$ bacteria inoculum is taken up in 400 µl of a 0.1M solution of sodium citrate containing 0.85 g of sodium chloride. 40 µl of sodium deoxycholate detergent (1%) are added. After incubating for 5 minutes at room temperature, 4 phenol-chloroform extractions are carried out (Maniatis et. al., 1982). The DNA is precipitated with ethanol. The pellet is taken up in 100 µl of sodium citrate buffer. This solution is sonicated by means of a 60W sonicator (Company: Bioblock, under the ref. C72442) using a "cuphorn" type probe (Company: Bioblock, under the ref. C72438) so as to obtain a population of fragments which are predominantly 1 Kilobase in size.

An aliquot, corresponding to 10$^8$ bacteria in 10 µl, is then identified by hybridization according to the following procedure. Into a microtiter plate (Trade name Nunc 439454), is deposited a solution of the capture oligonucleotide probe (probe SEQ ID NO 6) at 1 ng/µl, in 1× PBS (0.15M NaCl, 0.05M sodium phosphate, pH 7.0). The plate is incubated for 2 h at 37° C. and then washed 3 times with 300 µl of PBST (PBS+detergent of the trade mark TWEEN from the company MERCK). The target, consisting of 10 µl of sonicated total DNA, is mixed with 70 µl of PBS salmon buffer [3× PBS+10 µg/ml of salmon sperm DNA, (Sigma company, under the ref. D9156)] and 10 µl of 2N sodium hydroxide. The mixture is neutralized 5 minutes later by addition of 10 µl of 2N acetic acid. The mixture is added to the well, in addition to 50 µl of a solution of the peroxydase-labeled detection probe conjugate based on SEQ ID NO 7, at the concentration of 0.1 ng/µl, in PBS horse buffer [3× PBS+10% horse serum, (Company: BioMérieux SA, ref. 55842)].

The plate is incubated for 1 h at 37° C. and washed with 3×300 µl of PBS Tween [1× PBS+0.5% Tween 20 (Company: Merck, ref. 822184)].

100 µl of OPD substrate (ortho-phenylenediamine from Cambridge Medical Biotechnology ref./456) in a specific buffer (0.055M citric acid, 0.1M Na$_2$HPO$_4$, pH 4.93) at the concentration of 4 mg/ml to which are added, immediately for use, H$_2$O$_2$ at 30 volumes to 1/1000, are added per well. After reacting for 20 minutes, the enzymatic activity is blocked using 100 µl of 1N H$_2$SO$_4$ and the reading is performed in a microplate reader of the trademark Axia Microreader (Company BioMérieux SA) at 492 nm.

This system generates no background since the well containing the salmon DNA of the hybridization buffer, which is sonicated in the same manner as the DNA of the test strains, does not generate any signal. The results relating to specificity are the same as those obtained in stage 3. This application of a nonradioactive probe indicates that the specificity of the sequence of the invention is conserved regardless of the hybridization procedure used.

---

What is claimed:

1. A probe capable of specifically hybridizing with genomic DNA of *Streptococcus pneumoniae*, wherein the probe comprises the nucleotide sequence SEQ ID NO 3.

2. The probe as claimed in claim 1, wherein said nucleotide sequence SEQ ID NO 3 is flanked at its 5' end by a nucleotide sequence SEQ ID NO 2.

3. The probe as claimed in claim 1, wherein said nucleotide sequence SEQ ID NO 3 is flanked at its 3' end by a nucleotide sequence SEQ ID NO 4.

4. A method for the selective detection of *Streptococcus pneumoniae* strains in a biological sample containing bacteria, comprising:

providing genomic DNA of the bacteria contained in said sample, in the form of single-stranded fragments, exposing said fragments to a probe as claimed in claim 1, and determining whether hybridization occurs between the fragments and the probe, wherein *Streptococcus pneumoniae* strains that comprise any gene selected from the group consisting of mmsA, hexB, comA, aspS, lytA and ply will be detected.

5. The method as claimed in claim 4, further comprising, before exposing said DNA to said probe, exposing the genomic DNA to an enzymatic system and a pair of primers which is selected from the group consisting of the nucleotide sequences SEQ ID NO 8 to SEQ ID NO 21, thereby amplifying genomic DNA of *Streptococcus pneumoniae* in said sample.

6. The method as claimed in claim 4, further comprising, before exposing said DNA to said probe, exposing the genomic DNA to an enzymatic system and a pair of primers, said pair being selected from the nucleotide sequence pairs: (a) SEQ ID NO 8 and a member of the group consisting of SEQ ID NO 11, SEQ ID NO 13, SEQ ID NO 15, SEQ ID NO 17, SEQ ID NO 19 and SEQ ID NO 21; and (b) SEQ ID NO 10 and a member of the group consisting of SEQ ID NO 13, SEQ ID NO 15, SEQ ID NO 19 and SEQ ID NO 21, thereby amplifying genomic DNA of *Streptococcus pneumoniae* in said sample.

7. The method of claim 4, wherein said nucleotide sequence SEQ ID NO 3 is flanked at its 5' end by SEQ ID NO 2.

8. The method of claim 4, wherein said nucleotide sequence SEQ ID NO 3 is flanked at its 3' end by SEQ ID NO 4.

9. A primer for the specific amplification, by polymerization, of genomic DNA of *Streptococcus pneumoniae*, said primer having a nucleotide sequence selected from the group consisting of sequences SEQ ID NO 8 to SEQ ID NO 21.

10. A method of amplifying, by polymerization, of the genomic DNA of *Streptococcus pneumoniae*, comprising providing a primer as claimed in claim 9; and amplifying by polymerization the genomic DNA of *Streptococcus pneumoniae* with said primer.

11. A mixture containing a pair of primers comprising at least one primer as claimed in claim 9.

12. The mixture as claimed in claim 11, wherein the pair of primers is: (a) a primer of SEQ ID NO 8 and a member of the group consisting of a primer of SEQ ID NO 11, SEQ ID NO 13, SEQ ID NO 15, SEQ ID NO 17, SEQ ID NO 19 and SEQ ID NO 21; or (b) a primer of SEQ ID NO 10 and a member of the group consisting of a primer of SEQ ID NO 13, SEQ ID NO 15, SEQ ID NO 19 and SEQ ID NO 21.

13. A reagent comprising a pair of primers as claimed in claim 11.

14. A reagent comprising a pair of primers as claimed in claim 12.

* * * * *